United States Patent [19]

Müller et al.

[11] Patent Number: 5,194,225
[45] Date of Patent: Mar. 16, 1993

[54] CHROMATOGRAPHY COLUMN CARTRIDGE SYSTEM

[75] Inventors: Werner Müller, Heppenheim; Friedhelm Eisenbeiss, Weiterstadt; Jochen Kinkel, Guldental; Helmut Kohl, Darmstadt, all of Fed. Rep. of Germany

[73] Assignee: Merck Patent Gesellschaft Mit Beschrankter Haftung, Darmstadt, Fed. Rep. of Germany

[21] Appl. No.: 238,087

[22] Filed: Aug. 30, 1988

[30] Foreign Application Priority Data

Aug. 31, 1987 [DE] Fed. Rep. of Germany ....... 3729002

[51] Int. Cl.⁵ .................. G01N 30/02; B01D 15/08
[52] U.S. Cl. .......................................... 422/70; 422/81; 210/198.2; 210/656; 436/161
[58] Field of Search .............. 55/386; 210/198.2, 656; 73/23.1, 61.1 C; 422/68, 81, 101, 102, 70, 68.1; 436/89, 161

[56] References Cited

U.S. PATENT DOCUMENTS

| | | | |
|---|---|---|---|
| 3,855,130 | 12/1974 | Randau | 55/386 |
| 3,878,099 | 4/1975 | Ogle | 55/386 |
| 4,451,365 | 5/1984 | Sattler et al. | 210/198.2 |
| 4,603,114 | 7/1986 | Hood et al. | 422/68 |
| 4,711,764 | 12/1987 | Good | 422/70 |
| 4,737,284 | 4/1988 | Hauke et al. | 210/198.2 |
| 4,806,238 | 2/1989 | Satler et al. | 55/386 |

Primary Examiner—James C. Housel
Assistant Examiner—N. Bhat
Attorney, Agent, or Firm—Millen, White, Zelano and Branigan

[57] ABSTRACT

A chromatography column cartridge system comprised of an internal pressure-stable precision glass tube which can be filled with adsorbent and an external protection and/or temperature control jacket with column connection parts which can be screwed on. The column connection parts comprise a union nut which is screwed onto the protection and/or temperature control jacket. The union nut contains a milled nut and a plunger which seals the glass tube radially. Feed and discharge lines for the mobile phase pass through the column connection parts.

3 Claims, 4 Drawing Sheets

CHROMATOGRAPHY COLUMN CARTRIDGE SYSTEM

BACKGROUND OF THE INVENTION

The invention relates to a chromatography column cartridge system comprising an internal precision glass tube which can be filled with adsorbent and an external protection and/or temperature control jacket with column connection parts which can be screwed on.

Numerous glass columns for chromatography are already known. These usually have, at both ends, an external thread or a supporting nut with an internal or external thread, so that capillary connections for supply and removal of the eluant can be attached by means of a threaded stopper or a union nut.

The flanges, threads or ground glass edges obtained by appropriate working are a disadvantage with these glass columns, since experience has shown that these are the starting points for cracks. This means that these worked glass columns have a low pressure stability and very quickly fracture when the somewhat higher pressures, which are often necessary in liquid chromatography, are applied.

On the other hand, although chromatography columns of metal tubes are stable to pressure, they are not very suitable, for example, for biochromatography. Aqueous buffer systems or salt solutions are frequently used as the mobile phase in the separation of biomolecules, such as, for example, proteins, monoclonal antibodies, nucleic acids or subcellular units, which systems of solutions very rapidly attack the metal tubes.

There is therefore a need for a glass chromatography column which is stable to pressure and which in addition can also advantageously be used in accordance with the cartridge principle and at the same time is reliably sealed.

SUMMARY OF THE INVENTION

The invention thus relates to a chromatography column cartridge system comprising an internal pressure-stable precision glass tube which can be filled with adsorbent, an external protection and/or temperature control jacket with column connection parts which can be screwed on, which connection parts include a union nut which is screwed onto the protection and/or temperature control jacket, a milled nut with a plunger which seals the glass tube radially, and feed and discharge lines for the mobile phase.

The construction according to the invention has the advantage that the actual chromatography tube consists of a simple glass cylinder which has thick walls and has not been further worked after production. That is to say, the glass tube has no flange, no thread and also no ground edges, which, as experience has shown, are starting points for cracking and cause the pressure instability. The unworked glass tube is extremely stable and resistant to pressure, and the chromatography system according to the invention is thus even suitable for high pressure liquid chromatography under certain conditions.

Another important advantage is that the column can be used in accordance with the cartridge principle. That is to say, used adsorbent packings can be removed easily and quickly from the chromatography column cartridge system according to the invention with the entire glass tube and can be replaced by other tubes filled with new adsorbent.

Upon further study of the specification and appended claims, further objects and advantages of this invention will become apparent to those skilled in the art.

BRIEF DESCRIPTION OF THE DRAWINGS

The drawings show a preferred embodiment of the chromatography column cartridge system according to the invention. However, the principle according to the invention can be realized in various ways to suit specific requirements.

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 shows a section through the chromatography column cartridge system with the column connection parts screwed on;

DESCRIPTION OF THE PREFERRED EMBODIMENT

Figure 1:
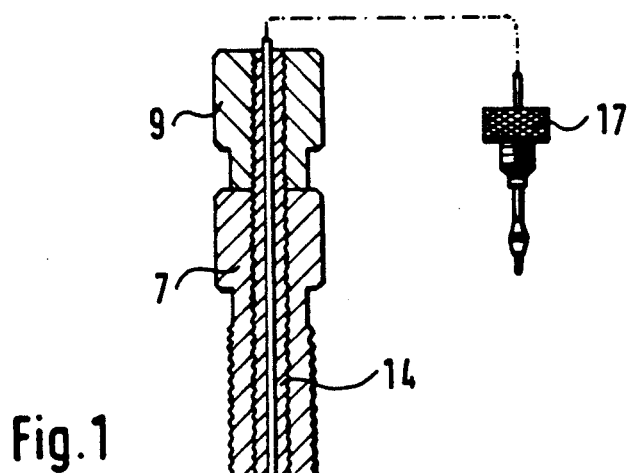
Figure 1:
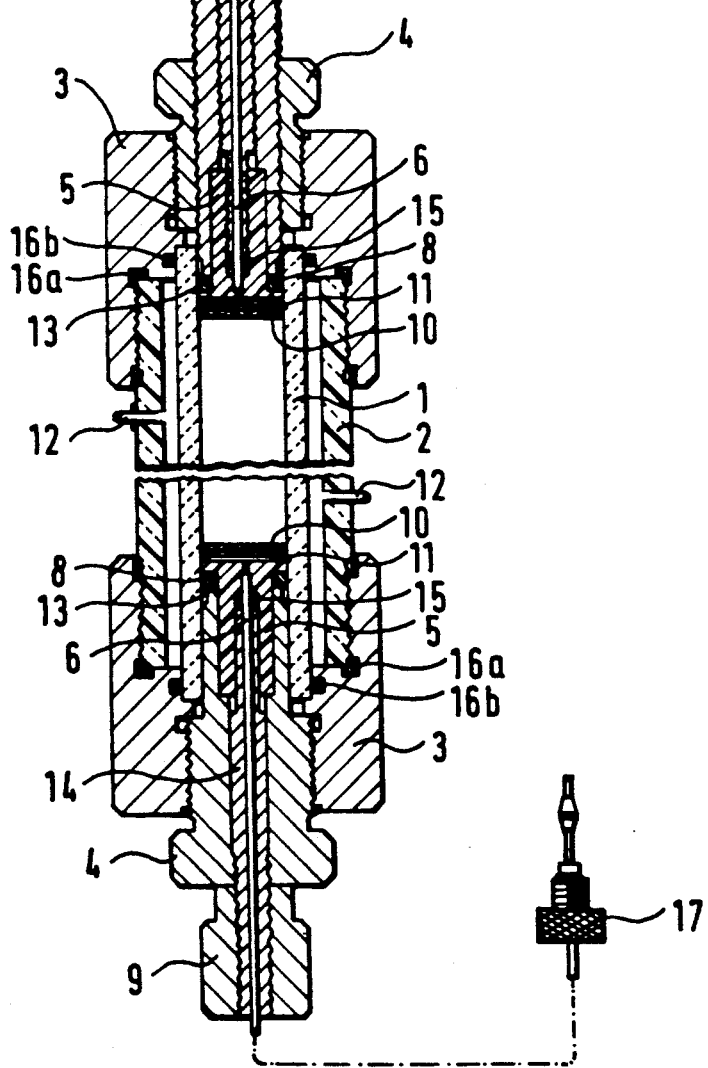
Figure 2:
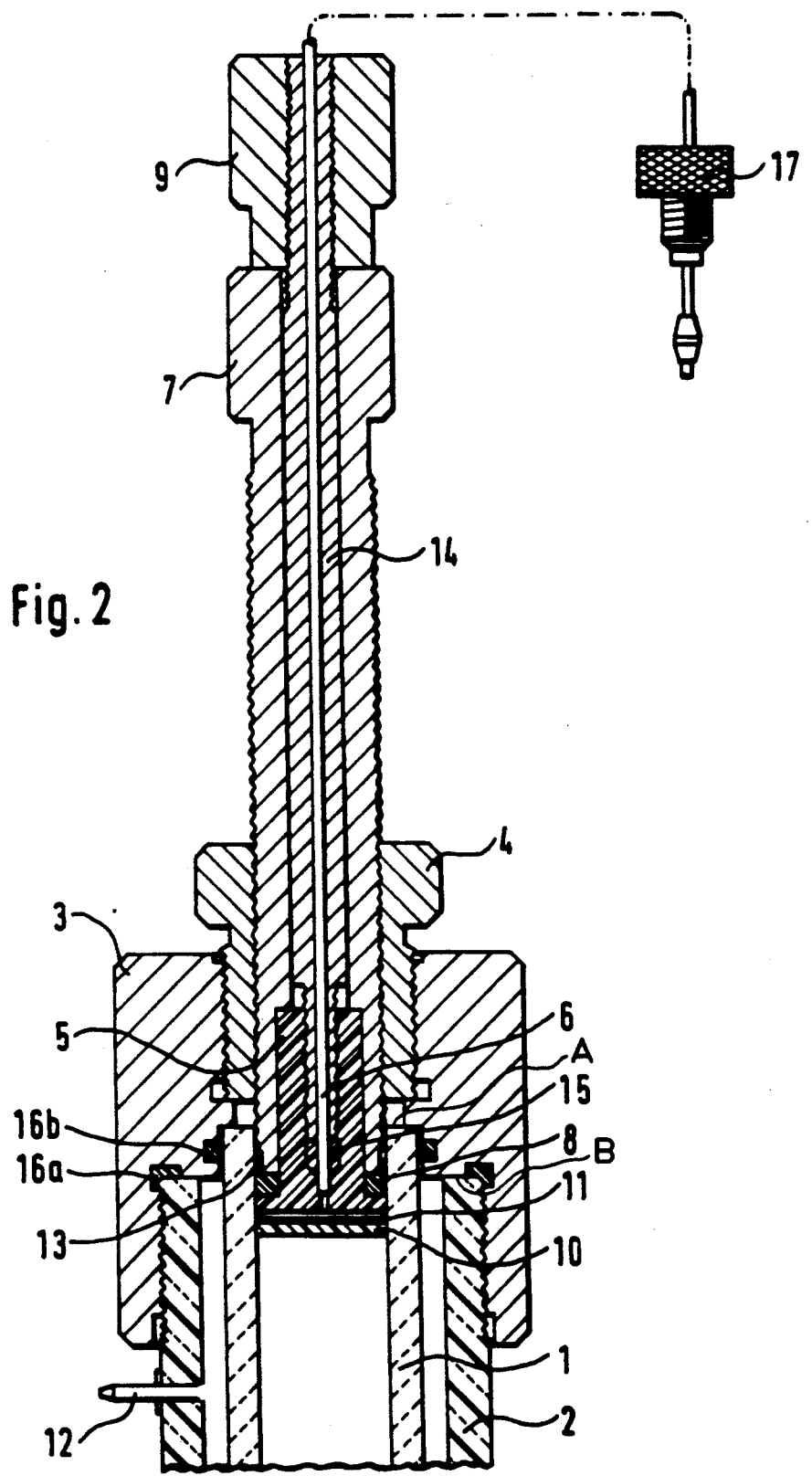
FIG. 2 is an enlarged section of a portion of the system of FIG. 1 showing a column connection part.

The column tube of glass 1 is usually filled with an adsorbent and is provided with a filter plate 10 and a fabric screen 11 for closing off the column bed.

The glass tube 1 can be produced from the customary glass materials, such as, for example, from borosilicate. The wall thickness of the glass cylinder is preferably in a range from 3 mm to 10 mm. The glass columns have dimensions which are customary for preparative liquid chromatography. Columns with a length of 10 cm to 150 cm and a diameter of 3 mm to 80 mm are usually employed.

The fabric screen, which consists of the generally known materials, such as, for example, polypropylene, glass fiber fleece or paper, guarantees perfect distribution of the sample to be separated.

The glass tube is contained in a protection jacket 2. This jacket is preferably designed as a temperature control jacket 2 with connections for hoses 12 which can circulate heat transfer fluid. The protection and/or temperature control jacket is preferably made of a transparent material, and particularly preferably consists of Plexiglas.

The transparency of the protection and/or temperature control jacket 2 has the great advantage that the progress of the chromatographic separation of, for example, colored substances can easily be observed.

The possibility of carrying out chromatographic separation at certain temperatures is a further great advantage of the system according to the invention, since there is often the need to carry out separations at reduced temperatures (for example, in the case of sensitive substances) or at elevated temperatures.

The column connection parts which can be screwed on and which connect and seal the internal glass tube and the external protection and/or temperature control jacket with one another preferably consist of the following individual parts.

The union nut 3 having first and second ends is screwed onto the protection and/or temperature control jacket with its first end axially spaced from the jacket and its second end overlying the jacket. It contains a milled nut 4 with a plunger 5 which, seals the glass tube radially, and feed and discharge lines 6 for the mobile phase. A shoulder A on union nut 3 abuts the glass tube 1 with a first land while a shoulder B on union nut 3 abuts the jacket 2. The shoulder A is also abutted by the end of milled nut 4 at a second land.

Figure 3:
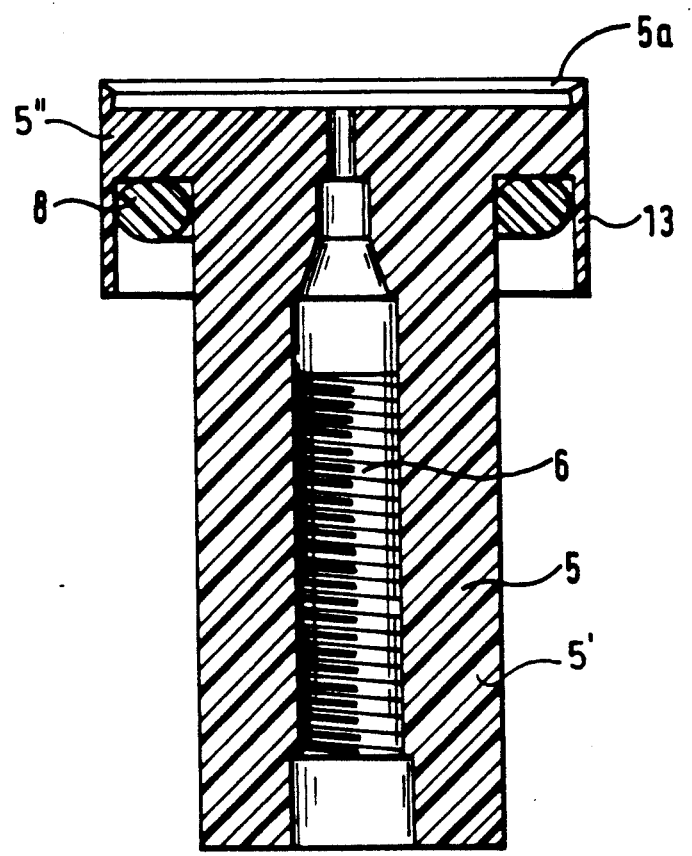
FIG. 3 shows a front piece of the plunger separately.

The plunger 5 has on its front face a conically shaped sealing lip (FIG. 3, 5a). This sealing lip lies closely to the glass tube 1 and automatically provides a seal in the radial direction when subjected to pressure. The plunger 5 has a first portion 5' and a second portion 5" which has a diameter greater than the first portion and approximates the inner diameter of the glass tube 1. Additional sealing is effected via O-rings 8 attached in the plunger 5. The plunger 5 is connected to a lock nut 9 (via steel tube 14) so that when the lock nut is screwed in, the O-rings 8 are deformed in the radial direction through the milled nut 4 lying in between as the pressure-transferring element. The rear sealing lip 13 of the plunger is thereby forced onto the glass tube in the radial direction, which leads to a complete, reliable seal.

The sealing lip 5a according to the invention which is attached to the front side of the plunger practically guarantees a seal which has no dead volume. The conically shaped sealing lip which lies tightly on the glass tube automatically presses onto the inside of the glass in the radial direction when pressure builds up in the column bed.

The internal diameter of the glass tube 1 and the diameter of the plunger 5 should therefore approximately coincide for optimum sealing.

One of the column connection parts which can be screwed on preferably contains a plunger of adjustable height. The milled nut 4 then additionally contains a threaded tube 7 with which the height adjustment of the plunger 5 is effected.

The feed and discharge lines for the mobile phase 6 are passed through steel tubes with threads 14 and fixed in the front piece of the plunger with the aid of plastic olives or inserts 15. Teflon hoses are preferably used. The end of the plunger 5 is abutted by internal shoulders C on the steel tubes 14.

The individual parts of the column connection parts are made of the customary materials for such parts, preferably of inert synthetic materials, for example, of polyamides or polyvinylidene fluorides. Preferably, further sealing rings 16a and 16b are also present in the union nut 3, in order to obtain an optimum seal between the glass tube, protection and/or temperature control jacket and column connection parts. The connections 17 are generally known screw connections for connecting the feed and discharge lines, for example, to the pump or detector system.

The seals 16a, 16b and 8 are preferably made of inert polymers, as is also the filter plate 10.

The glass tube filled with a chromatography packing can now be replaced easily and quickly by a separation tube with another adsorbent as required. This cartridge principle facilitates easy handling.

The separation column can, of course, also be lengthened as required by coupling pieces.

The chromatography column cartridge system according to the invention is extremely stable and resistant to pressure and can therefore also be used for high pressure liquid chromatography. For example, a glass tube with thick walls and of 1 cm internal diameter and 40 cm length can withstand an internal pressure of 300–400 bar.

Figure 4:
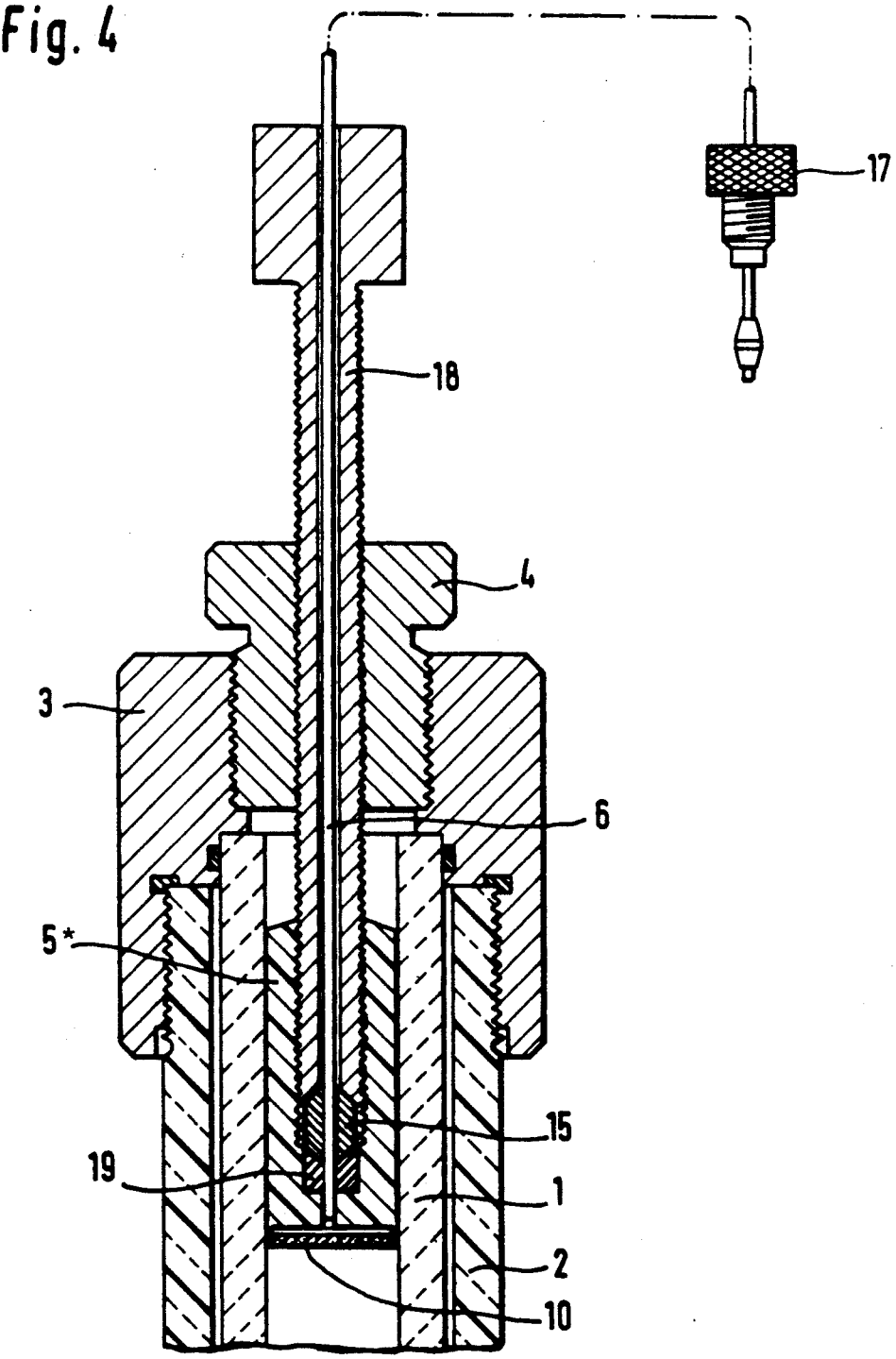
FIG. 4 is an enlarged section of another embodiment of the invention.

A further embodiment according to the invention is shown in FIG. 4. In this simplified embodiment also the plunger (5*) which is screwed into the milled nut (4) by the threaded tube (18) and thus also being of adjustable height, has on its front face the conically shaped sealing lip (5a) shown in FIG. 3, however, the O-rings and therefore also the lock nut for clamping the O-rings are absent in this case.

The sealing is effected solely by the sealing lip of the plunger. Optionally, a ring of metal (19), for example a ring of titanium, installed in front of the plastic olives (15) may contribute to an improved fixation of the feed and discharge lines (6) in the front piece of the plunger. The remaining numbers of FIG. 4 correspond to elements already described.

Above all this simplified embodiment also is suitable for analytical purposes in HPLC. The glass columns then have dimensions which are customary for analytical liquid chromatography.

The column systems according to the invention can thus be used in the entire chromatography field. These new chromatography column cartridge systems are preferably used in biochromatography. The chromatography column cartridge systems according to the invention meet the most important requirements of pressure stability, transparency of the column system, possibility of temperature control and inert materials which are imposed particularly frequently in this chromatography field.

An advantageous new chromatography column cartridge system which is generally applicable in chromatography is thus available.

From the foregoing description, one skilled in the art can easily ascertain the essential characteristics of this invention and, without departing from the spirit and scope thereof, can make various changes and modifications of the invention to adapt it to various usages and conditions.

The entire text of all applications, patents and publications, if any, cited above are hereby incorporated by reference.

What is claimed is:

1. A chromatography column and cartridge system for analyzing material in a solution comprising:

a glass tube for containing an adsorbent, the glass tube having a selected external diameter;

a transparent jacket having an internal diameter greater than the external diameter of the glass tube and having threaded end portions;

a union nut threaded to at least one of the threaded end portions of the transparent cylindrical jacket, the union nut having first and second ends and an internal cylindrical opening therethough which contains a shoulder in juxtaposition with the end of the glass tube, the internal cylindrical opening having threads disposed between the shoulder and the first end of the union nut;

a milled nut having a central bore, the milled nut being screwed into the internal cylindrical opening outboard of the shoulder and having an end surface in engagement with the shoulder;

a plunger having a bore therethrough and being made of a resilient material, the plunger having first and second portions, being received in both the glass tube and the bore of the milled nut and having a frusto-conical end disposed for sealing against the glass tube;

means for retaining the plunger in the glass tube, the retaining means comprising a first tube in threaded engagement with the bore of the milled nut and receiving the first portion of the plunger therein, the first tube having an end portion for applying an axial force against the second portion of the plunger to urge the second portion of the plunger radially against the inner wall of the glass tube, the retaining means further including a second tube slidably received within the first tube, the second tube having first and second threaded ends with the first end being in threaded engagement with a threaded bore within the plunger;

a locking nut threadably engaged with the second end of the second tube and abutting the end of the first tube to lock the second tube in place, and tube means passing through the plunger and in communication with the adsorbent in the glass tube for transporting the material to be analyzed by the chromatography system.

2. The system of claim 1 further including an O-ring seal disposed between the first end of the first tube and the second portion of the plunger.

3. The system of claim 2 further including inlet and outlet means in communication with a space between the jacket and glass tube for circulating heat transfer fluid so as to control the temperature within the glass tube.

* * * * *